United States Patent
Zou et al.

(10) Patent No.: US 11,142,513 B2
(45) Date of Patent: Oct. 12, 2021

(54) METHOD FOR SIMULTANEOUSLY PREPARING 2-ETHOXYPHENOL AND 1,3-BENZODIOXOLANE-2-ONE

(71) Applicant: Shanghai University, Shanghai (CN)

(72) Inventors: Xiujing Zou, Shanghai (CN); Gonglin Cheng, Shanghai (CN); Xueguang Wang, Shanghai (CN); Yankai Wang, Shanghai (CN); Xionggang Lu, Shanghai (CN); Weizhong Ding, Shanghai (CN)

(73) Assignee: SHANGHAI UNIVERSITY

( * ) Notice: Subject to any disclaimer, the term of this patent is extended or adjusted under 35 U.S.C. 154(b) by 0 days.

(21) Appl. No.: 17/028,290

(22) Filed: Sep. 22, 2020

(65) Prior Publication Data

US 2021/0261517 A1    Aug. 26, 2021

(30) Foreign Application Priority Data

Feb. 24, 2020 (CN) .......................... 202010113693.0

(51) Int. Cl.
C07D 317/64 (2006.01)
C07C 41/16 (2006.01)

(52) U.S. Cl.
CPC ............ *C07D 317/64* (2013.01); *C07C 41/16* (2013.01)

(58) Field of Classification Search
CPC ............................... C07D 317/64; C07C 41/16
See application file for complete search history.

(56) References Cited

FOREIGN PATENT DOCUMENTS

CN          101033177 A    *   9/2007

* cited by examiner

*Primary Examiner* — Matthew P Coughlin
(74) *Attorney, Agent, or Firm* — Onello & Mello, LLP

(57) ABSTRACT

The present invention belongs to the field of organic chemical synthesis, and provides a method for simultaneously preparing 2-ethoxyphenol and 1,3-benzodioxol-2-one. In the present invention, catechol and diethyl carbonate are subjected to a transesterification reaction under the action of a catalyst to obtain 2-ethoxyphenol and 1,3-benzodioxol-2-one. In the present invention, the combined selectivity of 2-ethoxyphenol and 1,3-benzodioxol-2-one can reach 97%. The method has the advantages of high conversion rate, high selectivity, high economic benefit, environmental friendliness and the like.

15 Claims, No Drawings

METHOD FOR SIMULTANEOUSLY PREPARING 2-ETHOXYPHENOL AND 1,3-BENZODIOXOLANE-2-ONE

CROSS REFERENCE TO RELATED APPLICATION

This application claims the priority of Chinese Patent Application No. 202010113693.0, filed on Feb. 24, 2020, entitled "Method for simultaneously preparing 2-ethoxyphenol and 1,3-benzodioxolane-2-one", which is incorporated herein by reference in its entirety.

TECHNICAL FIELD

The present invention belongs to the field of organic chemical synthesis, and particularly relates to a method for substantially simultaneously preparing 2-ethoxyphenol and 1,3-benzodioxol-2-one by a process of transesterification.

BACKGROUND ART 2-ethoxyphenol, also known as ethylguaiacol, CAS: 94-71-3, has the following properties: molecular formula: $C_8H_{10}O_2$; molecular weight: 138.16; melting point: 20-25° C.; and relative density: 1.076 g/cm$^3$. 2-ethoxyphenol is a fine chemical intermediate and chemical raw material used in formulating perfumes, agricultural chemicals, medicines, dyes and in other industries, with a wide range of uses. One of the most important uses is in the synthesis of the perfume ethyl vanillin. Ethyl vanillin has a stronger fragrance than vanillin, and it has become increasingly popular in the perfume industry due to the unique fragrance of ethyl vanillin. Moreover, ethyl vanillin has become a chemical that is in short supply owing to the increase in demand for ethyl vanillin year by year.

1,3-benzodioxol-2-one, CAS No. 2171-74-6, has the following properties: molecular formula: $C_7H_4O_3$; molecular weight: 136.1; density: 1.401 g/cm$^3$; boiling point: 180.8° C. (760 mmHg); flash point: 90.6° C.; refractive index: 1.584; and vapor pressure: 0.879 mmHg (25° C.). 1,3-benzodioxol-2-one and its derivatives are important organic chemical intermediates, which have wide uses in such technical fields as the fine chemicals industry, drug synthesis and the like, and they command high prices in the current market.

At present, the methods for synthesizing 2-ethoxyphenol and 1,3-benzodioxol-2-one have shortcomings such as more by-products and low yields. The raw materials and catalysts used in the prior art methods involve strong acids, strong bases, toxic and harmful compounds and the like, which could cause problems such as corrosion of process equipment, environmental pollution and so on.

SUMMARY OF THE INVENTION

In view of the above shortcomings of the prior art, an object of the present invention is to provide a method for substantially simultaneously preparing 2-ethoxyphenol and 1,3-benzodioxol-2-one by a process of transesterification, which has the advantages of a high conversion rate, high selectivity, high economic benefit, environmental friendliness and the like.

In order to achieve the above object, the present invention provides the following technical scheme:

The present invention provides a method for simultaneously preparing 2-ethoxyphenol and 1,3-benzodioxol-2-one, comprising the following steps:

performing the transesterification reaction of catechol and diethyl carbonate under the action of a suitable catalyst to obtain 2-ethoxyphenol and 1,3-benzodioxol-2-one.

In an embodiment of the invention, the molar ratio of the catechol to the diethyl carbonate is from about 1:2 to about 1:8.

In an embodiment of the invention, the amount of the catechol and the diethyl carbonate passing through a fixed-bed reactor per gram of the catalyst in the reactor per hour is about 0.15-1.5 ml.

In an embodiment of the invention, the catalyst is selected from the group consisting of one or more of aluminum phosphate, lanthanum phosphate, zirconium phosphate, cerium phosphate, zinc phosphate, calcium phosphate, magnesium phosphate and chromium phosphate.

In an embodiment of the invention, the transesterification reaction is carried out at a temperature of about 200-300° C.

In an embodiment of the invention, the transesterification reaction is performed under an inert atmosphere.

The invention provides a method for preparing, preferably for simultaneously or substantially simultaneously preparing, 2-ethoxyphenol and 1,3-benzodioxol-2-one. The raw material diethyl carbonate is non-toxic and harmless, and also low in price, thereby reducing the production cost. In the present invention, the combined selectivity of the reaction in the production of 2-ethoxyphenol and 1,3-benzodioxol-2-one can reach 97%, and the products obtained by the reaction are important intermediates in the fine chemicals industry, organic chemistry and drug synthesis, having high economic worth.

DETAILED DESCRIPTION OF THE EMBODIMENTS

The present invention provides a method for simultaneously preparing 2-ethoxyphenol and 1,3-benzodioxol-2-one, which has the advantages of high conversion rate, high selectivity, high economic benefit, environmental friendliness and the like.

The present invention provides a method for simultaneously preparing 2-ethoxyphenol and 1,3-benzodioxol-2-one, comprising a step of performing the transesterification reaction of catechol and diethyl carbonate under the action of a suitable catalyst to obtain 2-ethoxyphenol and 1,3-benzodioxol-2-one.

According to the present invention, the transesterification reaction is preferably performed in a fixed bed reactor. Specifically, the catechol and diethyl carbonate are mixed to configure a reaction liquid; the catalyst is placed in the fixed-bed reactor; and the temperature is raised to a transesterification reaction temperature under an inert atmosphere. Then, the reaction liquid is passed through the catalyst bed layer by a liquid sampling device at a controlled flow rate, and the mixed liquid of products and reactants is collected at the end of the fixed-bed reactor. In the present invention, the catechol and the diethyl carbonate are preferably fed into the fixed-bed reactor for the reaction by a constant-flow pump.

In an embodiment of the present invention, the molar ratio of the catechol to the diethyl carbonate is preferably from about 1:2 to about 1:8, more preferably from about 1:2 to about 1:5, and further preferably from about 1:3 to about 1:4.

In an embodiment of the present invention, the catalyst is preferably selected from the group consisting of one or more of aluminum phosphate, lanthanum phosphate, zirconium phosphate, cerium phosphate, zinc phosphate, calcium phosphate, magnesium phosphate and chromium phosphate;

more preferably from the group consisting of one or more of aluminum phosphate, lanthanum phosphate, magnesium phosphate and chromium phosphate; further preferably from the group consisting of chromium phosphate and/or magnesium phosphate.

In an embodiment of the present invention, the transesterification reaction is preferably carried out at a temperature of about 200-300° C., and more preferably at a temperature of about 230-250° C.

In an embodiment of the present invention, the desired process temperature is preferably obtained by raising the temperature of the transesterification reaction under an inert atmosphere. The inert atmosphere may specifically be argon or nitrogen.

In an embodiment of the present invention, the transesterification reaction is preferably performed at a flow rate of about 0.15-1.5 mL of the reaction liquid passing through the fixed-bed reactor per gram of the catalyst in the reactor per hour, and more preferably, the transesterification reaction is performed at a flow rate of about 0.15-1.0 mL of the reaction liquid passing through per gram of the catalyst in the reactor per hour.

The method for preparing 2-ethoxyphenol and 1,3-benzodioxol-2-one as provided by the present invention will be described in detail with reference to the following examples, but it should be understood that these examples are merely illustrative and should not be construed as limiting the scope of the present invention.

Example 1

In this example, catechol and diethyl carbonate were mixed in a molar ratio of 1:3 to configure a reaction solution. The lanthanum phosphate catalyst was placed in a fixed-bed reactor, and the temperature of the fixed-bed reactor was raised to 230° C. under a nitrogen atmosphere. The reaction liquid was fed into the fixed bed reactor by a constant-flow pump at the flow rate of 0.5 mL of the reaction liquid passing through per gram of the lanthanum phosphate catalyst per hour, so that the catechol and the diethyl carbonate were subjected to the transesterification reaction under the action of lanthanum phosphate catalyst. After the reaction was completed, the products 2-ethoxyphenol, 1,3-benzodioxol-2-one and the by-product o-diethoxybenzene were collected. In this example, the conversion rate of the reactant catechol was 75%, wherein the selectivity of 2-ethoxyphenol was 80%, the selectivity of 1,3-benzodioxol-2-one was 17%, the combined selectivity of 2-ethoxyphenol and 1,3-benzodioxol-2-one was 97%, the selectivity of by-product o-diethoxybenzene was 2%, and the selectivity of other by-products was about 1%. The 2-ethoxyphenol, 1,3-benzodioxol-2-one, and also the by-product o-diethoxybenzene obtained by the reaction of the present invention are important intermediates in the fine chemicals industry, organic chemistry, and drug synthesis, having high economic worth.

Example 2

In this example, catechol and diethyl carbonate were mixed in a molar ratio of 1:4 to formulate a reaction solution. The magnesium phosphate catalyst was placed in a fixed-bed reactor, and the temperature of the fixed-bed reactor was raised to 250° C. under an argon atmosphere. The reaction liquid was fed into the fixed bed reactor by a constant-flow pump at the flow rate of 1 mL of the reaction liquid passing through per gram of the magnesium phosphate catalyst per hour, so that the catechol and the diethyl carbonate were subjected to the transesterification reaction under the action of magnesium phosphate catalyst. After the reaction was completed, the products were collected. In this example, the conversion rate of the reactant catechol was 85%, wherein the selectivity of 2-ethoxyphenol was 86%, the selectivity of 1,3-benzodioxol-2-one was 11%, the combined selectivity of the former and the latter was 97%, the selectivity of by-product o-diethoxybenzene was 2%, and the selectivity of other by-products was about 1%. The 2-ethoxyphenol, 1,3-benzodioxol-2-one, and also the by-product o-diethoxybenzene obtained by the reaction of the present invention are important intermediates in the fine chemicals industry, organic chemistry, and drug synthesis, having high economic worth.

From the above examples, it can be seen that the method for simultaneously or substantially simultaneously preparing 2-ethoxyphenol and 1,3-benzodioxol-2-one provided by the present invention has the following properties: the raw material diethyl carbonate is non-toxic and harmless, and also low in price, thereby reducing the production cost. In the present invention, the combined selectivity of 2-ethoxyphenol and 1,3-benzodioxol-2-one can reach 97%, and the products obtained by the reaction are important intermediates in the fine chemicals industry, organic chemistry and drug synthesis, having high economic worth.

While the present invention has been particularly shown and described with reference to preferred embodiments thereof, it will be understood by those skilled in the art that various improvements and changes may be made therein without departing from the spirit and scope of the invention, and all of these are intended to be within the scope of this invention.

What is claimed is:

1. A method for preparing 2-ethoxyphenol and 1,3-benzodioxol-2-one, comprising the following steps:
    performing the transesterification reaction of catechol and diethyl carbonate under the action of a catalyst to obtain 2-ethoxyphenol and 1,3-benzodioxol-2-one.

2. The method according to claim 1 for preparing 2-ethoxyphenol and 1,3-benzodioxol-2-one, wherein the molar ratio of the catechol to the diethyl carbonate is about 1:2 to about 1:8.

3. The method according to claim 1 for preparing 2-ethoxyphenol and 1,3-benzodioxol-2-one, wherein the transesterification reaction is carried out in a fixed-bed reactor containing a catalyst and wherein the combined amount of the catechol and the diethyl carbonate passing through the fixed-bed reactor per gram of the catalyst per hour is about 0.15-1.5 ml.

4. The method according to claim 1 for preparing 2-ethoxyphenol and 1,3-benzodioxol-2-one, wherein the transesterification reaction is carried out in the presence of a catalyst selected from the group consisting of one or more of aluminum phosphate, lanthanum phosphate, zirconium phosphate, cerium phosphate, zinc phosphate, calcium phosphate, magnesium phosphate and chromium phosphate.

5. The method according to claim 3 for preparing 2-ethoxyphenol and 1,3-benzodioxol-2-one, wherein the catalyst is selected from the group consisting of one or more of aluminum phosphate, lanthanum phosphate, zirconium phosphate, cerium phosphate, zinc phosphate, calcium phosphate, magnesium phosphate and chromium phosphate.

6. The method according to claim 1 for preparing 2-ethoxyphenol and 1,3-benzodioxol-2-one, wherein the transesterification reaction is carried out at a temperature of about 200-300° C.

7. The method according to claim 6 for preparing 2-ethoxyphenol and 1,3-benzodioxol-2-one, wherein the transesterification reaction is performed under an inert atmosphere.

8. The method according to claim 1 wherein the 2-ethoxyphenol and 1,3-benzodioxol-2-one reaction products are produced substantially simultaneously.

9. A method for simultaneously preparing 2-ethoxyphenol and 1,3-benzodioxol-2-one, comprising the following steps:
performing the transesterification reaction of catechol and diethyl carbonate under the action of a catalyst to obtain 2-ethoxyphenol and 1,3-benzodioxol-2-one.

10. The method according to claim 9 for simultaneously preparing 2-ethoxyphenol and 1,3-benzodioxol-2-one, wherein the molar ratio of the catechol to the diethyl carbonate is about 1:2 to about 1:8.

11. The method according to claim 9 for simultaneously preparing 2-ethoxyphenol and 1,3-benzodioxol-2-one, wherein the transesterification reaction is carried out in a fixed-bed reactor containing a catalyst and wherein the combined amount of the catechol and the diethyl carbonate passing through the fixed-bed reactor per gram of the catalyst per hour is about 0.15-1.5 ml.

12. The method according to claim 9 for simultaneously preparing 2-ethoxyphenol and 1,3-benzodioxol-2-one, wherein the transesterification reaction is carried out in the presence of a catalyst selected from the group consisting of one or more of aluminum phosphate, lanthanum phosphate, zirconium phosphate, cerium phosphate, zinc phosphate, calcium phosphate, magnesium phosphate and chromium phosphate.

13. The method according to claim 11 for simultaneously preparing 2-ethoxyphenol and 1,3-benzodioxol-2-one, wherein the catalyst is selected from the group consisting of one or more of aluminum phosphate, lanthanum phosphate, zirconium phosphate, cerium phosphate, zinc phosphate, calcium phosphate, magnesium phosphate and chromium phosphate.

14. The method according to claim 9 for simultaneously preparing 2-ethoxyphenol and 1,3-benzodioxol-2-one, wherein the transesterification reaction is carried out at a temperature of about 200-300° C.

15. The method according to claim 14 for simultaneously preparing 2-ethoxyphenol and 1,3-benzodioxol-2-one, wherein the transesterification reaction is performed under an inert atmosphere.

* * * * *